United States Patent [19]

Sommer et al.

[11] 4,261,929
[45] Apr. 14, 1981

[54] PROCESS OF PRODUCING N-ACYLAMINOMETHANE PHOSPHONIC ACIDS

[75] Inventors: Klaus Sommer, Heidelberg; Guenter Raab, Laudenbach, both of Fed. Rep. of Germany

[73] Assignee: Benckiser-Knapsack GmbH, Ladenburg am Neckar, Fed. Rep. of Germany

[21] Appl. No.: 50,087

[22] Filed: Jun. 19, 1979

[30] Foreign Application Priority Data

Jul. 1, 1978 [DE] Fed. Rep. of Germany ....... 2829046

[51] Int. Cl.$^3$ ............................................... C07F 9/38
[52] U.S. Cl. .................................... 260/502.5; 546/22
[58] Field of Search ...................................... 260/502.5

[56] References Cited

U.S. PATENT DOCUMENTS

| | | | |
|---|---|---|---|
| 2,304,156 | 12/1942 | Englemann et al. | 260/502.5 |
| 4,009,204 | 2/1977 | Krueger et al. | 260/502.5 |
| 4,098,814 | 7/1978 | Sommer et al. | 260/502.5 |

*Primary Examiner*—Joseph E. Evans
*Attorney, Agent, or Firm*—Schwartz, Jeffrey, Schwaab, Mack, Blumenthal & Koch

[57] ABSTRACT

The present invention is concerned with the novel and highly advantageous process of producing N-acylaminomethanephosphonic acid in a one-step process by reacting a acylonitrile with formaldehyde or a formaldehyde-yielding compound and phosphorous acid in the presence or absence of the solvent at an elevated temperature, preferably at a temperature between about 60° C. and the boiling point of the mixture. The reaction may be carried with or without a polar aprotic solvent and/or an acidic catalyst.

14 Claims, No Drawings

PROCESS OF PRODUCING N-ACYLAMINOMETHANE PHOSPHONIC ACIDS

BACKGROUND OF THE INVENTION

1. Field of the Invention

The present invention relates to a novel and highly advantageous process of producing acylamino methane phosphonic acids and their salts, to compounds obtained by said process, to a method of using said compounds, and to compositions useful for such purpose.

2. Description of the Prior Art

U.S. Pat. Nos. 2,304,156; 2,328,358; and 2,862,882 describe processes of making acylamino methane phosphonic acids. According to said patents, N-methylol compounds of carboxylic acid amides are reacted with phosphorous trichloride. The reaction mixture is then hydrolyzed by the addition of acetic acid or hydrochloric acid. The starting methylol compounds are obtained as described in Ann. 343 (1905) 210 by reaction of amides with formaldehyde or by decomposition of the corresponding chloromethyl compounds according to U.S. Pat. No. 2,131,362.

SUMMARY OF THE INVENTION

It is one object of the present invention to provide a simple and highly advantageous process of producing N-acylaminomethane phosphonic acids, said process using starting materials which can be more readily prepared than the starting materials used for the known processes.

Another object of the present invention is to provide acylaminomethane phosphonic acids prepared according to such a process.

A further object of the present invention is to provide a method of using such acylaminomethane phosphonic acids and their salts.

In principle the novel and advantageous process according to the present invention comprises the step of reacting a nitrile with formaldehyde and phosphorus acid. Preferred nitriles are the nitriles of the formula R—CN 

in which
R indicates hydrogen, lower alkyl, such as methyl or ethyl, cycloalkyl such as cyclohexyl, hydroxy lower alkyl, such as hydroxyethylene, alkylene such as ethylene, or aryl, such as phenyl.

The nitriles are reacted with formaldehyde and phosphorus acid at elevated temperature. The starting nitriles are in general more easily obtainable than the corresponding acid amides as used when carrying out the known processes. Thus the resulting N-acylaminomethane phosphonic acids of the formula R.CO.NH.CH$_2$.PO$_3$H$_2$ 

can be obtained in one single reaction step and in a higher yield than heretofore obtainable.

Other advantages of this novel process are that the nitriles used as starting materials are more readily obtainable than the corresponding acylamines of the prior art and that the hydrolysis step as required in the known processes is omitted.

The process according to the present invention is preferably carried out by preparing a mixture of the nitrile, formaldehyde, and phosphorus acid in the molar proportion of 1:2:1 to 1:1:1 and more advantageously in the molar proportion of 1:1:1, and heating said mixture at a temperature between about 60° C. and about 100° C. for about three to four hours.

Nitriles which have proved to be especially suitable for the present invention are the readily available nitriles such as acetonitrile, propionitrile, butyronitrile, cyclohexyl cyanide, and hydroxypropionitrile. It is, of course, also possible to use other nitriles such as, for instance, oxydiacetonitrile, succinyl dinitrile, adipinyl dinitrile, cyanoacetic acid ester, methacrylnitrile, crotonitrile, benzonitrile, chlorobenzonitrile, tolylcyanide, glycinonitrile, benzylcyanide, cyanofurane, cyanopyridines, aminotrisacetonitrile, and others for the reaction of the present invention.

In place of formaldehyde, there can be used compounds capable of splitting off formaldehyde under the reaction conditions such as trioxane or paraformaldehyde as well as aqueous solutions thereof. When using an aqueous solution of formaldehyde or a formaldehyde-yielding compound, it is also possible to employ as the third reaction compound a phosphorous trihalogenide such as phosphorus trichloride which is hydrolyzed under such reaction conditions to phosphorus acid.

The reaction of this invention can be carried out in the presence or in the absence of solvents. Suitable solvents are preferably polar, aprotic solvents. Especially useful solvents have proved to be dimethoxyethane, dimethyl diglycol ether, diethyl diglycol ether, dioxane, and tetramethylene sulfone. In place of said solvents there can also be used the nitriles employed as reactants. In this case the amounts of the nitriles added may be 1.5 to 5.0 times the stoichiometric amount.

Furthermore, it has been found that the reaction can be carried out in a highly rational manner and within a short reaction time by adding to the reaction mixture small amounts of an acidic compound such as concentrated sulfuric acid, hydrogen halides, or phosphoric acid.

It is also possible to use, in place of the nitriles and formaldehydes, hexahydro-1,3,5-triacyl triazines (N-triacyl triazines) as they are obtained by reacting nitriles with formaldehyde according to Journ. Am. Chem. Soc. vol. 70 (1948), page 3079. The reaction of such compounds with phosphorous acid proceeds in a similar manner as when reacting mixtures of nitriles, formaldehyde, and phosphorus acid.

Acylaminomethane phosphonic acids can be hydrolyzed to aminomethane monophosphoric acids. While direct reaction of ammonia or, respectively, ammonium chloride with phosphorus acid and formaldehyde yields mainly nitrilotrismethane phosphonic acid and only small amounts of mono- and diphosphonic acids, it is possible to produce relatively pure aminomethane monophosphonic acid by hydrolysis of the above-mentioned acylaminomethane phosphonic acids.

DESCRIPTION OF THE PREFERRED EMBODIMENTS

The following examples serve to illustrate the present invention without, however, limiting the same thereto.

EXAMPLE 1

82 g of aqueous phosphorous acid and 32 g of trioxane are dissolved in 200 cc of acetonitrile. 5 cc of phosphorus trichloride are added to said solution. The resulting mixture is heated to boiling under reflux for about two hours. A highly viscous oil separates as a result of the reaction. Unreacted acetonitrile is distilled off. The residue is dissolved in a small amount of water. Addition of acetone precipitates therefrom a white crystalline product which is filtered off and dried at 60° C. in a water jet vacuum. About 100 g of N-acetylaminomethane phosphonic acid are obtained. By thin layer chromatographic investigation of the filtrate it was found that, in addition to phosphorous acid, the solution still contained some additional N-acetylaminomethane phosphonic acid and also another phosphonic acid which apparently is N-acetylimino-bis-methane phosphonic acid.

Analysis of the reaction product: Found: C: 23.7%, N: 9.3%, P: 20.4%; Calculated: C: 23.54%, N: 9.15%, P: 20.23%

EXAMPLE 2

82 g of anhydrous phosphorus acid, 41 g of acetonitrile, and 5 cc of phosphorous trichloride are dissolved in 150 cc of anhydrous dimethyl diglycol. The solution is heated to 100° C. 30 g of paraformaldehyde are added portion by portion thereto. After boiling the mixture under reflux for three hours, the reaction is completed. The solvent is removed by decanting from the highly viscous residue (reaction residue). Thereupon the viscous paste is heated with 50 cc of concentrated hydrochloric acid under reflux for 24 hours. The heated mixture is concentrated by evaporation in a water jet vacuum in order to remove acetic acid split off thereby and the excess hydrochloric acid. The resulting residue is taken up in a small amount of water. The aminomethane phosphonic acid obtained thereby is caused to crystallize by the addition of a small amount of ethanol.

75 g of aminomethane phosphonic acid are obtained thereby after drying at about 60° C. over phosphorus pentoxide.

Analysis after recrystallization of the acid: Found: C: 11.1%, N: 12.5%, P: 27.9%, Calculated: C: 10.81%, N: 12.61%, P: 27.90%.

EXAMPLE 3

20.5 g of acetonitrile, 15.0 g of trioxane, 41 g of phosphorous acid, and 1 cc of sulfuric acid are dissolved in 100 cc of dimethoxyethane. The solution is heated to boiling under reflux for three hours. A slightly yellowish oil separates thereby. The solvent is removed by distillation. The oily residue is extracted three times, each time with 70 cc of ethyl acetate in order to remove excess and unreacted phosphorous acid, and is dried over phosphorous pentoxide at about 60° C. The yield of the resulting reaction product amounts to 68 g.

Analysis of the acid after extraction with acetone and drying it: Found: C: 23.8%, N: 9.0%, P: 20.2%; Calculated: C: 23.54%, N: 9.15%, P: 20.23%.

EXAMPLE 4

41 g of acetonitrile and 137 g of phosphorous trichloride are heated in 150 cc of dioxane to a temperature between 40° C. and 50° C. 78.9 g of a 37% formaldehyde solution are added drop by drop to the heated mixture within three hours. The temperature is kept thereby between about 60° C. and about 70° C. The reaction mixture is heated to boiling under reflux for two more hours. Thereby a viscous paste separates. Said paste is identified as N-acetylaminomethane phosphonic acid.

EXAMPLE 5

21.3 g of 1,3,5-triacetyl triazine are heated with 24.6 g of phosphorous acid in 50 cc of tetramethylene sulfone at a temperature between about 80° C. and 90° C. A viscous, yellowish oil separates after a certain period of time from the reaction mixture. Said oil is purified and caused to crystallize as described in the preceding examples.

35 g of colorless crystals are obtained. Said crystalline compound corresponds to N-acetylaminomethane phosphonic acid according to its analysis.

In place of acetonitrile as used in the preceding examples, there may also be employed stoichiometric amounts of other nitriles as they have been mentioned hereinabove.

TABLE

| Example | Nitrile or triazane used | N-acylaminomethane phosphonic acid obtained |
|---|---|---|
| 6 | propionitrile | N-propionylaminomethane phosphonic acid |
| 7 | 1,3,5-triacryl-s-triazane | N-acrylaminomethane phosphonic acid |
| 8 | 1,3,5-trimethacryl-s-triazane | N-methacrylaminomethane phosphonic acid |
| 9 | butyronitrile | N-butyrylaminomethane phosphonic acid |
| 10 | cyclohexylcyanide | N-cyclohexanoylamino-methane phosphonic acid |
| 11 | 1,3,5-tribenzotriazane | N-benzoylaminomethane phosphonic acid |
| 12 | 1,3,5-tripyridinoformyl-triazane | N-pyridinoformylamino-methane phosphonic acid |

Of course, many changes and variations in the starting material used, especially in the acylating agent employed, in the reaction conditions such as temperature and duration, in the solvents and adjuvants added, in the manner of working up, purifying and crystallizing the reaction products, and the like may be made by those skilled in the art in accordance with the principles set forth herein and in the claims annexed thereto.

The salts of the N-acylaminomethane phosphonic acids are prepared by neutralization of the acids with carbonates or bicarbonates.

What is claimed is:

1. A process for producing N-acylaminomethane phosphonic acids, comprising the step of simultaneously reacting at an elevated temperature
  a first reactant comprising
    (A.) a mixture of
      (1.) a nitrile having the formula

R—CN wherein R is a member selected from the group consisting of hydrogen, lower alkyl, lower alkenyl, aryl, cyclo-lower alkyl and hydroxyl lower alkyl, and
      (2.) formaldehyde or a compound which yields formaldehyde under the reaction conditions, or
    (B.) a reaction product of said nitrile and formaldehyde, said reaction product comprising a triacyl-1,3,5-triazine compound, and
  a second reactant comprising phosphorus acid or a compound which yields phosphorous acid under the reaction conditions, whereby there is produced an N-acylaminomethane phosphonic acid having the formula

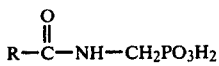

wherein R has the meaning stated above.

2. A process according to claim 1, wherein said first reactant comprises a mixture of said nitrile and a formaldehyde-yielding compound selected from the group consisting of trioxane and paraformaldehyde.

3. A process according to claim 1, wherein said first reactant comprises a reaction product of said nitrile and formaldehyde.

4. A process according to claim 1, wherein said step of reacting is carried out in a solvent.

5. A process according to claim 1, wherein said step of reacting out with the addition of an acidic agent.

6. A process according to claim 5, wherein the acidic agent comprises an agent selected from the group consisting of sulfuric acid, a hydrogenhalide, and phosphoric acid.

7. A process according to claim 4, wherein said solvent comprises a polar, aprotic solvent.

8. A process according to claim 7, wherein said solvent comprises a solvent selected from the group consisting of dimethoxyethane, dimethylglycol, diethyl diglycol, dioxane, and tetramethylene sulfone.

9. A process according to claim 1, wherein said compound which yields phosphorous acid comprises a phosphorous trihalogenide and water.

10. A process according to claim 1, consisting reacting a mixture consisting essentially of said nitrile, formaldehyde and phosphorous acid in molar proportion of between about 1:2:1 and about 1:1:1.

11. A process according to claim 1, wherein said elevated temperature is between about 60° C. and 100° C.

12. A process according to claim 1, wherein said reaction step is carried out for a period of between about 3 and 4 hours.

13. A process according to claim 10, wherein said nitrile is selected from the group consisting of acetonitrile, propionitrile, butyronitrile, cyclohexyl cyanide and hydroxypropiontrile.

14. A process according to claim 4, wherein an excess amount of said nitrile comprises said solvent, said excess amount comprising from about 1.5 to 5 times the stoichiometric amount required for reaction.

* * * * *

UNITED STATES PATENT OFFICE
CERTIFICATE OF CORRECTION

Patent No. 4,261,929    Dated April 14, 1981

Inventor(s) Klaus SOMMER and Guenter RAAB

It is certified that error appears in the above-identified patent and that said Letters Patent are hereby corrected as shown below:

Column 1, line 13, kindly delete "2,328,358" and insert instead -- 2,328,353 --.

Column 1, line 17, kindly delete "phosphorous" and insert instead -- phosphorus --.

Column 1, line 40, kindly delete "phosphorus" and insert instead -- phosphorous --.

Column 1, line 51, kindly delete "phorus" and insert instead -- phorous --.

Column 1, line 63, kindly delete "acylamines" and insert instead -- acylamides --.

UNITED STATES PATENT OFFICE
CERTIFICATE OF CORRECTION

Patent No. 4,261,929     Dated April 14, 1981

Inventor(s) Klaus SOMMER and Guenter RAAB

It is certified that error appears in the above-identified patent and that said Letters Patent are hereby corrected as shown below:

Column 1, line 68, kindly delete "phosphorus" and insert instead -- phosphorous --.

Column 2, line 23, kindly delete "phosphorous" and insert instead -- phosphorus --.

Column 2, line 24, kindly delete "phosphorus" and insert instead -- phosphorous --.

Column 2, line 42, kindly delete "triazines" and insert instead -- triazanes --.

Column 2, line 43, kindly delete "triazines" and insert instead -- triazanes --.

Column 2, line 48, kindly delete "phosphorus" and insert instead -- phosphorous --.

Column 2, line 50, kindly delete "monophosphoric" and insert instead -- monophosphonic --.

Column 2, line 52, kindly delete "phosphorus" and insert instead -- phosphorous --.

Column 3, line 20, kindly delete "phosphorus" and insert instead -- phosphorous --.

Column 3, line 21, kindly delete "phosphorous" and insert instead -- phosphorus --.

UNITED STATES PATENT OFFICE
CERTIFICATE OF CORRECTION

Patent No. 4,261,929  Dated April 14, 1981

Inventor(s) Klaus SOMMER and Guenter RAAB

It is certified that error appears in the above-identified patent and that said Letters Patent are hereby corrected as shown below:

Column 3, line 59, kindly delete "phosphorous" and insert instead -- phosphorus --.

Column 4, line 3, kindly delete "triazine" and insert instead -- triazane --.

Column 4, line 56, kindly delete "hydroxyl" and insert instead -- hydroxy --.

Column 4, line 64, kindly delete "phosphorus" and insert instead -- phosphorous --.

Column 5, line 17, after "of reacting" kindly insert -- is carried --

Column 6, line 6, kindly delete "consisting" and insert instead -- comprising --.

Column 6, line 19, kindly delete "hydroxy-propiontrile" and insert instead -- hydroxypropionitrile --.

Signed and Sealed this

Seventeenth Day of November 1981

[SEAL]

Attest:

GERALD J. MOSSINGHOFF

Attesting Officer  Commissioner of Patents and Trademarks